United States Patent [19]

MacFadyen

[11] 4,028,378

[45] June 7, 1977

[54] FATTY AND BENZOIC ACID ESTERS OF ETHOXYLATED HYDANTOINS SUBSTITUTED OR NOT IN THE 5-POSITION

[75] Inventor: Donald Edward MacFadyen, Williamsport, Pa.

[73] Assignee: Glyco Chemicals, Inc., Greenwich, Conn.

[22] Filed: Nov. 17, 1975

[21] Appl. No.: 632,320

Related U.S. Application Data

[63] Continuation-in-part of Ser. No. 419,497, Nov. 27, 1973, abandoned.

[52] U.S. Cl. .............................. 260/309.5; 8/189; 252/8.8; 252/358; 260/45.8 R
[51] Int. Cl.² ..................................... C07D 233/72
[58] Field of Search .......................... 260/309.5

[56] References Cited

UNITED STATES PATENTS

| 3,676,454 | 7/1972 | Vida | 260/309.5 |
| 3,821,098 | 6/1974 | Garratt et al. | 260/309.5 |
| 3,852,302 | 12/1974 | Habermeier | 260/309.5 |
| 3,904,644 | 9/1975 | Jaeger | 260/309.5 |

FOREIGN PATENTS OR APPLICATIONS

| 38-19987 | 9/1963 | Japan | 260/309.5 |

OTHER PUBLICATIONS

Wolf et al. Chem. Abst. 1970, vol. 73, No. 57285h.

Primary Examiner—Natalie Trousof

[57] ABSTRACT

Esters of 1,3-dihydroxyethyl group-containing-hydantoins having the structural formula

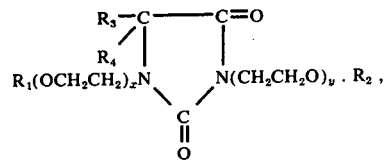

wherein each of $R_3$ and $R_4$ separately is hydrogen, lower alkyl, cycloalkyl, or alkoxy and when either or each of $R_3$ and $R_4$ is alkyl, cycloalkyl or alkoxy, they jointly have at most 7 carbons, or $R_3$ and $R_4$ jointly are the divalent tetramethylene or pentamethylene chain; either one of $R_1$ and $R_2$ is hydrogen, and the other one or each of them is acetoyl, benzoyl, isostearoyl, oleoyl, linoleoyl, linolenoyl, or saturated fatty acyl having from 2 to about 22 carbons or a mixture of saturated fatty acyl groups having from 8 to about 22 carbons or a mixture of any of said saturated fatty acyl groups with any of oleoyl, linoleoyl and linolenoyl, palmitoleoyl and myristoleoyl; and each of $x$ and $y$ varies from each of them being 1 to their sum averaging from 2 to about 100; and mixtures of any of said esters.

32 Claims, No Drawings

FATTY AND BENZOIC ACID ESTERS OF ETHOXYLATED HYDANTOINS SUBSTITUTED OR NOT IN THE 5-POSITION

This application is a continuation-in-part of my copending application Ser. No. 419,497 filed Nov. 27, 1973 and now abandoned.

This invention is that of certain carboxylic acid mono- or di-esters of a 1,3-dihydroxyethyl group-containing hydantoin, which esters have the formula

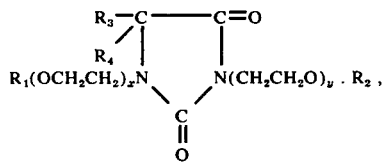

wherein each of $R_3$ and $R_4$ separately is hydrogen, straight or branched chain lower alkyl as methyl, ethyl, n-propyl, isopropyl, n-butyl, isobutyl, n-amyl, isoamyl or hexyl, cycloalkyl as cycloamyl or cyclohexyl, or alkoxy as methoxy, ethoxy or propoxy, and when either or each of $R_3$ and $R_4$ is alkyl, cycloalkyl or alkoxy, they jointly have at most 7 carbons, or $R_3$ and $R_4$ jointly are the divalent tetramethylene or pentamethylene chain; either one of $R_1$ and $R_2$ is hydrogen, and the other one or each of them is benzoyl, isostearoyl (as below identified), oleoyl, linoleoyl, linolenoyl, or saturated fatty acyl having from 2 to about 22 carbons or a mixture of saturated fatty acyl groups having from 8 to about 22 carbons or a mixture of any of said saturated fatty acyl groups with any of oleoyl, linoleoyl, linolenoyl, palmitoleoyl and myristoleoyl; and each of $x$ and $y$ varies from each of them being 1 to their sum averaging from 2 to about 100.

The invention includes also:
i. mixtures of any of the esters described in the just preceding paragraph,
ii. such esters or mixtures of them, wherein each of $R_3$ and $R_4$ is methyl and each of $x$ and $y$ varies from each of them being one to their sum averaging from 2 to about 20,
iii. and of these last esters or mixtures of them, esters and mixture of them wherein each of $x$ and $y$ is one;
iv. and of the mixture of esters of the foregoing subdivision (iii), a mixture of esters wherein each of $R_1$ and $R_2$ is a mixture of the acyl groups of the fatty acids contained in the commercial white oil grade of oleic acid; and
v. of this last mixture of esters, those wherein from about 80 to about 88.5 percent of the acyl groups $R_1$ and $R_2$ are those of the total "oleic" acids of that commercial oleic acid and the remainder of the acyl groups are those of the saturated fatty acids of that commercial oleic acid; and
vi. of this just preceding mixture of esters, a mixture of them wherein the commercial white oil grade of oleic acid consists essentially of about 72.5% of 9-cis-octadecenoic acid, about 8.6% of linoleic acid, about 5.7% of palmitoleic acid, about 1.4% of myristoleic acid, about 0.9% of stearic acid, about 2.1% of heptadecanoic acid, about 5% of palmitic acid, about 3.2% of myristic acid and about 0.5% of lauric acid.

Also part of the invention are vii. those esters or mixtures of them as described in the foregoing subdivision (ii), wherein the sum of $x$ and $y$ averages from about 5 to about 20, and of these
viii. a mixture of esters, wherein each of $R_1$ and $R_2$ is a mixture of the acyl groups of the fatty acids contained in one of (a) the commercial grade hydrogenated coconut oil fatty acids, (b) the commercial grade stearic acid, or (c) commercial white oil grade of oleic acid; and
ix. of the foregoing mixture of esters (viii), a mixture of esters wherein each of $R_1$ and $R_2$ is a mixture of the acyl groups contained in the commercial grade of the hydrogenated coconut oil fatty acids containing about 55% lauric acid, about 15% myristic acid, about 8% each of stearic acid and palmitic acid, about 7% caprylic acid, about 6% capric acid, and about 1% oleic acid; and
x. of the foregoing mixture of esters (ix), a mixture of esters wherein the sum of $x$ and $y$ averages from about 19 to 22.

Also included in the mixture of esters (viii) is
xi. a mixture of esters, wherein each of $R_1$ and $R_2$ is a mixture of the acyl groups of the fatty acids of the commercial white oil grade of oleic acid, and the ester content has (a) as its major portion the two mono-esters (i) the one wherein $R_2$ is hydrogen and (ii) the one wherein $R_1$ is hydrogen, and (b) as its minor portion the di-ester having these acyl groups as each of $R_1$ and $R_2$ and, when the molar ratio of the total of the acyl groups of the mono-ester and the di-ester to that of the hydantoin moiety is less than one, then together with the correspondingly small residual unreacted starting hydantoin.

Then of this mixture of esters (xi), there is included
xii. a mixture of esters, wherein the sum of $x$ and $y$ averages from about 4 to 7, and the minor portion of the ester content consists essentially of said di-ester;
xiii. a mixture of esters, wherein the sum of $x$ and $y$ averages from about 9 to 12, and the minor portion of the ester content consists essentially of said di-ester; and
xiv. a mixture of esters, wherein the sum of $x$ and $y$ averages from about 14 to 17, and the minor portion of the ester content consists essentially of said di-ester.

The invention also includes of the mixture of esters (viii) above,
xv. a mixture of esters, wherein from about 80 to about 88.5 percent of the acyl groups $R_1$ and $R_2$ are those of the total "oleic" acids of that commercial oleic acid and the remainder of the acyl groups are those of the saturated fatty acids of that commercial oleic acid; and
xvi. from the foregoing mixture of esters in (xv) a mixture of esters, wherein the commercial white oil grade of oleic acid consists essentially of about 72.5% of 9-cis-octadecenoic acid, about 8.6% of linoleic acid, about 5.7% of palmitoleic acid, about 1.4% of myristoleic acid, about 0.9% of stearic acid, about 2.1% of heptadecanoic acid, about 5% of palmitic acid, about 3.2% of myristic acid and about 0.5% of lauric acid.

Of the mixture of esters embraced in the subdivision (iii) above, the invention includes also
xvii. a mixture of esters wherein each of $R_1$ and $R_2$ is a mixture of the acyl groups contained in a commercial grade of hydrogenated coconut oil fatty acids; and xviii. of this just last mixture of esters there is included a mixture of esters wherein the mixture of said acyl groups contains about 55% lauric acid, about 15% myristic acid, about 8% each of stearic acid and palmitic acid, about 7% caprylic acid, about 6% capric acid, and about 1% oleic acid.

Of the mixture of esters of subdivision (viii) above, the invention includes also xix. a mixture of esters wherein the mixture of acyl groups is that of the fatty acids of a commercial grade of stearic acid;

xx. a mixture of the subdivision (xix) mixture, wherein the sum of $x$ and $y$ averages from 8 to about 12;

xxi. of this mixture (xx), a mixture of esters wherein the sum of $x$ and $y$ averages about 11.5;

xxii. of the mixture of esters (xxi), a mixture of esters wherein the commercial grade of stearic acid is the so-called 70% commercial stearic acid; and xxiii. of the mixture of esters (xxii), a mixture of esters, wherein said 70% commercial stearic acid contains about 68% of stearic acid, 2% of margaric acid, 26.5% of palmitic acid, 0.5% pentadecanoic acid, 2% of myristic acid, and 1% of oleic acid.

Of the mixture of esters of subdivision (iv) above, the invention includes also xxiv. a mixture of esters wherein the acyl groups are those of the fatty acids of a commercial white oil grade of oleic acid and the molar ratio of the total of the acyl groups to that of the ethoxylated hydantoin moiety is about 2 to 1; and xxv. of the mixture of esters (xxiv), a mixture of esters wherein from about 80 to about 88.5 percent of the acyl groups are those of the total "oleic" acids of said commercial oleic acid.

Of the mixture of esters of subdivision (xi) above, the invention includes xxvi. a mixture of esters wherein the molar ratio of the total of the acyl groups to that of the ethoxylated hydantoin moiety is from about 1 to about 2 moles of acyl groups per mol of said hydantoin moiety, xxvii. of the mixture of esters of subdivision (xxvi) above, a mixture of esters wherein the sum of $x$ and $y$ averages from 4 to 7; and xxviii. of the just preceding mixture of esters, a mixture of esters wherein the sum of $x$ and $y$ averages about 6.6.

The invention also includes of the mixture of esters in subdivision (xxvi) above, xxix. a mixture of esters wherein the sum of $x$ and $y$ averages from about 9 to 12, and xxx. of the just preceding mixture of esters (xxix), a mixture of esters wherein the sum of $x$ and $y$ averages about 11.8.

Of the mixture of esters in subdivision (xxvi) above, the invention also includes (xxxi). A mixture of esters wherein the sum of $x$ and $y$ averages from about 14 to 17; and xxxii. of the just preceding mixture of esters, also a mixture of esters wherein the sum of $x$ and $y$ averages about 16.2.

The mono- and di-esters of the invention are variedly useful as thermally stable plasticizers and lubricants for incorporation into films and other forms of plastics such as polyvinyl pyrollidone, for spin lubricants for various textile fibers such as the cellulose fibers as cotton and for nylon, enhanced antistatic agents as for nylon and textile fibers, and as dispersing agents for various materials such as formaldehyde dimethyl-hydantoin resins, and as emulsifying agents, for example, oil-in-water with the esters wherein $R_1$ and/or $R_2$ are acyl having at least 10 carbons and water in oil with the esters wherein $R_1$ and/or $R_2$ are acyl with less than 10 carbons.

The so-called isostearic acid providing the above-mentioned isostearoyl group is the mixture of acids obtained after separating the dimer acids produced in the dimerization of linoleic acid and subsequent hydrogenation of this dimerization product, as is described in U.S. Pat. No. 3,527,705 (column 1 lines 48–67).

The esters of the invention are prepared by esterifying the selected starting dihydroxyethyl group-containing hydantoins under esterifying conditions with 1 or 2 moles of whichever of benzoic acid or the fatty acid, whose acyl group is to be added, to provide respectively the corresponding mono-, sesqui- or di-ester. To make up for any possible loss of the starting substituted-hydantoin by volatilization during the esterification, it sometime is desirable to use the starting substituted-hydantoin material in a slightly excess molar ratio such as up to about 6% molar excess.

The esterification conditions include using a catalytically effective amount of an esterification catalyst such as hypophosphorous acid, and heating the reaction batch to an esterification initiation temperature such as from about 110° to 150° C., and by suitable known means separating the water formed, gradually increasing the temperature to about 220° to 250° C. and continuing the heating until withdrawn test samples indicate the esterification to be substantially complete.

The dihydroxyethyl-group-containing starting hydantoins are prepared by ethoxylating hydantoin or any desired of the above 5-mono- or di-substituted hydantoins under suitable ethoxylation conditions with the required number of moles of ethylene oxide to provide the desired average sum for $x$ and $y$ in the earlier above structural formula, for example, by (i) mixing (a) any applicable starting hydantoin (of the type herein described) in (b) an amount of dioxane, polychlorethane or other compatible solvent for it, sufficient to dissolve the starting hydantoin at the below elevated temperature and superatmospheric pressure reaction conditions, together with (c) an ethoxylation-catalyzing effective amount of a compatible ethoxylation catalyst and in a confined reaction zone (e.g. an agitator-equipped autoclave), (ii) heating the thus confined admixed reaction materials at an elevated temperature of at least about 50° to dissolve the starting hydantoin, (iii) at the elevated temperature introducing the required number of moles of ethylene oxide under increased pressure, and causing the ethylene oxide and dissolved starting hydantoin to react together under those reaction conditions, and until the ethylene oxide is consumed, as noted by a distinctly sharp drop in the reaction pressure.

The quantity of the ethylene oxide introduced into the confined reaction zone should be below that which can cause runaway ethoxylation under the reaction conditions involving operating temperature and pressure, and specific catalyst and its amount.

The ratio of the starting hydantoin to the amount of solvent used is not critical. The maximum is that amount of starting hydantoin which could be dissolved at the reaction operating conditions in the quantity of the solvent used, even if they form a mixture slurry at the initial ambient mixing temperature. However, that concentration is not essential.

It is possible, if needed, to use by weight as little as one part of the starting hydantoin to about 10 or 11 parts of the solvent used. A practical operating ratio can be by weight from about 40 to about 55 parts of the hydantoin to from about 60 to 45 parts of solvent. A generally practical proportion for good operation is about equal parts by weight of the starting hydantoin and solvent.

Any effective ethoxylation-catalyzing catalyst can be used in an ethoxylation-catalyzing effective amount. The catalyst beneficially should be one which is at least partially soluble in the solvent reaction medium. Generally, at least with dioxane as the solvent, an alkali metal hydroxide, such as sodium hydroxide and advantageously potassium hydroxide (because of its greater solubility than sodium hydroxide) in a convenient concentration aqueous solution is very well effective, beneficially as a 45% KOH aqueous solution.

Other alkaline catalysts such as tertiary amines also can be used and possibly more readily with 1,1,2-trichlorethane as the solvent, although the alkali metal hydroxide particularly the KOH catalyst also can be used with this solvent. Boron trifluoride can be used as a non-alkaline catalyst. The amount of catalyst to use can be relatively small, because it need be merely sufficient adequately to catalyze the reaction, i.e. give a practically satisfactory reaction rate, for example, as indicated by the stability of the operating temperature.

Thus, while one can use as little as about 0.5% of catalyst based on the weight of the starting hydantoin, the maximum amount used need not exceed about 1.5%. About 1.0% of the starting hydantoin weight is generally suitable, particularly as presently indicated with the 45% KOH aqueous solution. With that KOH solution the 1.0% of it then amounts to 0.45% actual KOH based on the starting hydantoin weight.

The respective amounts of the selected starting hydantoin and solvent for it, conveniently in equal weights, together with the amount of catalyst to be used are charged in any order into a pressure vessel, e.g. an autoclave, equipped with an agitator and jacketed for steam and water selectively, and having a fluid feed inlet to its interior. The stirred charge mixture is heated by indirect heat exchange to at least about 50° C., better yet to at least about 60° and beneficially to about 70° and even to about the solvent's boiling point, to dissolve the starting hydantoin. It is advantageous then to purge the autoclave with nitrogen introduced through the fluid feed inlet to remove oxygen from the system.

The ethylene oxide to be used then can be introduced while the reaction solution is at some temperature between 120° and 150°, although the ethoxylation can be conducted at any level in the range of 50° to 200°, and at an (autoclave) internal pressure of 35 to 50, or even to 65, pounds per square inch (psig). To avoid runaway addition condensation, it is advantageous to introduce the ethylene oxide at a controlled rate.

For example, as the ethylene oxide is consumed and the pressure drops to about 35 to 45 psig., a further portion of it is introduced until the pressure again reaches 50 to 65 psig., and the temperature again maintained at 140° to 150° until the pressure again drops to about 35 to 45 psig. Repeated further portions of ethylene oxide are added as the pressure drops to about 35–45 psig. to raise it to about 50 to 65 psig., until the required weight of ethylene oxide, to provide the required substitution on the ring nitrogens, is consumed.

The reaction mass then is transferred to a still wherein the solvent is distilled off and recovered. The catalyst may be neutralized or not, beneficially before the distillation, depending on the specific use to be made of the end product.

While the reaction is described above as carried out up to 150°, when required under particular conditions the reaction can be conducted at any higher temperature and corresponding pressure, but below such temperature and pressure at which the hydantoin ring can be degraded (i.e. split) under the reaction conditions, or undesirable color which cannot be removed by the ordinarily available means, is left in the end product. Thus, 200° can be considered a practical maximum temperature and up to 400 psig. as maximum pressure.

These starting dihydroxyethyl-group-containing hydantoins also can be prepared as described in British patent specifications Nos. 1,290,728 (Example C page 8, Example F page 9, Example J page 11 and Example M page 12) and 1,290,729.

The starting di-hydroxyethyl group-containing hydantoins are represented by the structural formula shown in the second paragraph of this specification but with each of $R_1$ and $R_2$ being hydrogen. These starting 1,3-dihydroxyethyl group-containing hydantoins are illustrated by, but not restricted to, N,N'-dihydroxyethyl-5,5-dimethylhydantoin, and the products of the formula shown in the first paragraph of this specification, wherein each of $R_3$ and $R_4$ is methyl, each of $R_1$ and $R_2$ is hydrogen and $x + y$ averages 5, 6, 10, 15, 20 or 50, and also all of these same products but wherein $R_3$ is methyl and $R_4$ is ethyl, as well as those wherein either or each of $R_3$ and $R_4$ is any of the other alkyl, alkoxy or polymethylene groups or all as described in that first paragraph of the specification. In addition, the starting bis-dihydroxyethyl group-containing hydantoins can be any of their commercial grades such as of N,N'-dihydroxyethyl-5,5-dimethylhydantoin which consists essentially of (a) from about 80% to about 87% of 1,3-di(beta-hydroxyethyl)-5,5-dimethylhydantoin, (b) from about 5% to about 15% of triethoxylated-5,5-dimethylhydantion, and (c) from about 9% to none of the mono-hydroxyethyl-5,5-dimethylhydantoin.

As indicated by the earlier above broad description of the ester products of the invention, the required carboxylic acid reactant can be benzoic acid or any of the fatty acids having from 2 to about 22 carbons such as the saturated fatty acids as any of those from acetic acid to caproic acid, caprylic acid, capric acid, lauric acid, myristic acid, pentadecanoic acid, palmitic acid, margaric acid, stearic acid, arachidic acid and behenic acid, the above-identified so-called isostearic acid, as well as the unsaturated fatty acids such as oleic, linoleic, linolenic, palmitoleic and myristoleic acids, as well as various commercially available or blended mixtures of any of the saturated fatty acids having from 8 to about 22 carbons, and mixtures of any of them with any or all of oleic, linoleic and linolenic acids.

The carboxylic acid mono-, sesqui- and di-esters of the dihydroxyethyl group-containing hydantoins of this invention are illustrated by, but not restricted to, the following examples (wherein all temperatures are centigrade):

EXAMPLE 1

Dioleate of
1,3-Di(Beta-Hydroxyethyl)-5,5-dimethylhydantoin 426 grams (i.e. gm.) (1.53 moles) of the so-called "white oil" commercial oleic acid of average molecular weight 278 (80–88% total "oleic" acids) and 174 gm. (0.82 mole) of commercial grade 1,3-di(beta-hydroxyethyl)-5,5-dimethylhydantoin, average molecular weight 215 as calculated from its hydroxyl value determination (containing about 85.7% of this N,N'-dihydroxyethyl compound, about 13% of the derivative wherein $x + y$ of the earlier above structural formula averages 3, and 1.3% of the mono-hydroxyethyl compound, all calculated on a water-free and ethylene glycol free basis) were charged together with 0.6 gm. of hypophosphorous acid as catalyst (as a 50% aqueous solution of it) into a 1-liter, 3-necked, round bottom flask equipped with a stirrer, thermometer, and a Dean-Stark water removal apparatus, and with provision for maintaining a nitrogen blanket over the reaction mixture. The flask was jacketed with the well known 'Glas-Col' heating jacket. Heat was applied to, while agitating, the reaction batch and water of esterification started to evolve at 110°–120°. Heating was continued while maintaining the reaction temperature at 220°, and the extent of completion of esterification was observed by periodically withdrawing small aliquot samples and determining their hydroxyl number and acid value.

After heating for about 8 hours at 220°, the hydroxyl number was found to be less than 10 and the acid value less than 5, the esterification was considered to be substantially complete. The reaction mixture was cooled at 70° and then 0.2% of its weight of 35% hydrogen peroxide was admixed with it. The resulting deodorized reaction mixture was filtered with the use of a diatomaceous earth filter aid to provide 556.3 gm. of the resulting dioleate of dihydroxyethyl dimethylhydantoin (yield 97.2% of theory), analysis showed it to have acid value 3.9, hydroxyl value 9.5, and saponification value 155.4.

EXAMPLE 2

Distearate of
1,3-di(beta-hydroxyethyl)-5,5-dimethylhydantoin (2 to 1.06 molar ratio of acid to diol)

2,456 gm. (9.15 moles) of the so-called 55% commercial grade stearic acid (containing from about 50 to 57% stearic acid, about 41% palmitic acid, about 2% of myristic acid, 1–2% of margaric acid, a trace of lauric acid and less than 0.5% of pentadecanoic acid) and 1,044 gm. (4.86 moles) of the same commercial grade 1,3-di(beta-hydroxyethyl)-5,5-dimethylhydantoin were charged together with 3.5 gm. of hypophosphorous acid as catalyst (same solution as in Example 1) into a 1-liter, 3-necked round bottom flask equipped with a small vertical reflux condenser, stirrer and provision for blanketing and sparging the reaction mixture with a constant flow of nitrogen.

Heat was applied (as in Example 1) and while agitating under a gentle and continuous nitrogen stream the temperature was raised to 120°, and esterification product water was removed with the nitrogen stream and continued as the temperature was slowly increased over 9 hours at 220°.

Progress of the esterification was followed by periodic removal of small aliquot samples of the reaction batch and analyzing for acid value and hydroxyl number. The esterification was considered substantially complete when analysis showed an acid value of 4 and hydroxyl number of 8.7. The reaction batch then was cooled to 70° and decolorized by admixing 35% hydrogen peroxide to the extent of 0.2% by weight of the batch and filtered through a filter aid (all as in Example 1).

The resulting 3,312.8 gm. of the distearate ester of the commercial N,N'-dihydroxyethyl-5,5-dimethylhydantoin (99.3% yield of theory) showed an acid value of 4, hydroxyl value of 8.8 and saponification value of 159.

EXAMPLE 3

Distearate of
1,3-Di(Beta-Hydroxyethyl)-5,5Di-methylhydantoin
(2.1 to 1 molar ratio of acid to diol)

435 gm. (1.61 moles) of the commercial grade stearic acid (of the 55% type, average molecular weight 270) and 165 gm. (0.77 mole) of the commercial N,N'-dihydroxyethyl-5,5-dimethylhydantoin, and 1.2 gm. of a commercial grade of a technical toluene sulfonic acid catalyst (Witco Chemical Corp., N.Y., 'Ultra TX Acid', 95% minimum modified toluene sulfonic acids) were charged into a 3-necked flask equipped and heated as in Example 2. Esterification product water evolved slowly at 130° and continued as the reaction temperature was raised uniformly to 205° over 9 hours. The esterification was considered complete when a sample of the reaction batch showed an acid value of 8.6 and hydroxyl value of nil. The batch was cooled to 70° and there bleached with 35% hydrogen peroxide (as in Example 2) for 30 minutes. The color was improved only slightly from Gardner color scale 11 to 9. Using a common clay filter aid, the reaction batch was filtered and yielded 546 gm. (95.4% of theory) of the distearate of the N,N'-dihydroxyethyl-5,5-dimethylhydantoin, showing acid value of 8.6, hydroxyl value nil, and saponification value 160.6.

EXAMPLE 4

"Mono"-oleate of
1,3-(beta-hydroxyethyl)-5,5-di-methylhydantoin (1 to 1.05 molar ratio of acid to diol)

1,937 gm. (6.91 moles) of "white oil" commercial oleic acid (average molecular weight 280) and 1,563 gm. (7.27 moles) of the commercial 1,3-di(beta-hydroxyethyl)-5,5-dimethylhydantoin of Example 1 together with 3.5 gm. of hypophosphorous acid as catalyst (same solution as in Example 1) were charged into a 5-liter, 3-necked round bottom flask equipped with stirrer, an inlet for nitrogen for sparging use, and a 4-inch vertical condenser attached to a Claisen head connected to a horizontal condenser for removal of water and return of low-boiling substances to the reaction mixture.

Heat was applied (by a 'GLAS-COL' heating jacket) to the reaction batch while agitating it under a continuous gentle nitrogen stream, and evolution of esterification product water started at 125°. The esterification was deemed to be substantially complete when, after 10 hours of heating with increasing temperature to finally 250°, a sample of the reaction batch showed an acid value of 1 and a hydroxyl value of 112. The batch then was cooled to 70° and was deodorized by admixture, with continued stirring, of 35% hydrogen peroxide over one hour to the extent of 0.2% by weight of the batch.

Admixing the thus treated reaction batch with the filter aid as in Example 1 and filtering it provided 3,320.3 gm. (98.4% of theory) of the mono-oleate of the commercial grade of 1,3-di(beta-hydroxyethyl)-5,5-dimethylhydantoin having acid value 0.97, hydroxyl value 112.2, saponification value 125.7, and Gardner scale color less than 1.

EXAMPLE 5

Dilaurate Of
1,3-Dihydroxyethyl-5,5-dimethylhydantoin (1.975 to 1 ratio of acid to diol)

387 Pounds (1.86 moles) of commercial hydrogenated coconut fatty acids (the 55% lauric acid type containing about 55% lauric acid, 15% myristic acid, 8% each of of stearic and palmitic acids, 7% caprylic acid, 6% capric acid and 1% oleic acid), 213 pounds (0.942 moles) of commercial grade 1,3-di(beta-hydroxyethyl)-5,5-dimethylhydantoin (average molecular weight 226), together with 0.6 pound of hypophosphorous acid (50% aqueous solution) as catalyst, were charged into a 100 gallon stainless steel (pilot size) esterifier equipped with turbine agitator, heating jacket (for use with a DOWTHERM heating medium), internal stainless steel coils for heating (e.g. with high pressure steam) or cooling, and with means at the bottom of the internal reactor surface for introducing a stream of blanketing gas (e.g. carbon dioxide), and also to remove, condense, collect and measure esterification water product.

While agitating and maintaining the reaction mixture under a $CO_2$ blanket (at 50 cubic feet per hour) both steam and hot DOWTHERM were used to heat the reaction batch rapidly to 220°. At this point to moderate the reaction rate, the heat flow was controlled to increase the temperature at 10° per hour over about 3 hours to 250°. When the extent of water evolution indicated that the esterification reached over 90%, samples of the batch were removed at hourly intervals for acid value test.

After about 6 hours at 250° an acid value of 4.5 indicated that the esterification was substantially complete.

The reaction batch was cooled to 70° and deodorized by addition of 35% hydrogen peroxide (to the extent of 0.2% of the batch) and heating for an hour at 110°. After admixing a diatomaceous earth filter aid and filtering, the 508 pounds yield (89.7% of theory) of the resulting so-called dilaurate (mixed fatty acids) of N,N'-dihydroxyethyl-5,5-dimethylhydantoin product showed an acid value of 4.5, saponification value 187.5, hydroxyl value 16.5 and Gardner scale color 3+. Treating that product with 0.05% of its weight of a solution of 50% sodium chlorite in water for an hour at 70° to 110° reduced the color to 1+.

EXAMPLE 6

Mono-(mixed)Caprate-Caprylate of
1,3Dihydroxyethyl-5,5-dimethylhydantoin (1 to 1.06 ratio of mixed acids to diol)

1,394 gm. (9.23 moles) of a blend of about 30% of capric acid and about 70% of caprylic acid (average molecular weight 151) and 2,106 gm. (9.8 moles) of the commercial 1,3-di(beta-hydroxyethyl)-5,5dimethylhydantoin of Example 1 were charged into a 2-liter, 3-necked round bottom flask equipped with stirrer, a Dean-Stark esterification "head", and provision for blanketing the reaction mixture with nitrogen gas. 3.5 gm. of hypophosphorous acid (as a 50% aqueous solution) was admixed with the charge.

The reaction batch was heated (by a GLAS-COL heating jacket) cautiously to minimize volatilization of any of the fatty acids. Elimination of esterification product water was carried out carefully by means of the Dean-Stark apparatus by keeping the water product in this "head" at sufficient height to let any floating oil in it be returned to the flask, thereby almost constantly returning any volatilized fatty acid to the reaction batch. The heating was continued until 90% of the theoretical water product was removed.

The heating then was increased to raise the reaction temperature over a period of about 6 hours to 250° (in the flask), when a sample of the reaction batch showed an acid value of 1.6. The esterification was deemed to be substantially complete and was cooled to 70°, and deodorized by admixing 35% hydrogen peroxide to the extent of 0.2% by weight of the reaction batch and heating for 1 hour. Admixing a filter aid and filtering (all as in Example 1) provided 3267.2 gm. (98.0% of theory) of the resulting mono-(mixed caprate and caprylate) of the starting 5,5-dimethylhydantoin diol, with acid value 1.6, saponification value 158.8 and hydroxyl value 166.4.

EXAMPLE 7

"Mono"-acetate of
1,3-(dihydroxyethyl)-5,5-dimethylhydantoin (1 to 1.06 molar ratio of acid to diol)

125 gm. (2.08 moles) of glacial acetic acid and 475 gm. (2.21 moles) of the same commercial grade 1,3-di(beta-hydroxyethyl)-5,5-dimethylhydantoin as used in Example 1 above together with 2.4 gm. of hypophosphorous acid (as 50% aqueous solution) were charged into a 1-liter, 3-necked round bottom flask equipped with stirrer, a 12-inch fractionating column (packed with Goodloe meshed screen) connected to a horizontal condenser, and provision for nitrogen gas sparging.

Heat was applied (e.g. by GLAS-COL heating jacket) and esterification product water evolution was controlled to maintain the temperature at the head of the fractionating column below 110°. When 95% of the theoretical water product was collected (measured by the total volume of condensate), a small sample of the reaction batch showed an acid value of 1.3 and the esterification was considered substantially complete.

The reaction batch was cooled to 70°, and deodorized by heating at 110° for an hour after admixing 35% hydrogen peroxide to the extent of 0.4% by weight of the reaction batch. After admixing a filter aid and filtering as in Example 1, there was obtained a 511 gm. (90.8% of theory) yield of the "mono"-acetate of the starting dihydroxyethyl-5,5-dimethylhydantoin, with acid value 1, hydroxyl value 220.7 and saponification value 213.9.

EXAMPLE 8

Diacetate of
1,3-(dihydroxyethyl)-5,5-dimethylhydantoin (2.8 to 1 molar ratio of acid to diol)

207 gm. (3.45 moles) glacial acetic acid and 264 gm. (1.23 moles) of the commercial dihydroxyethyl-5,5- dimethylhydantoin of Example 1 together with 0.5 gm. of hypophosphorous acid (as the 50% aqueous solution) were charged into a 500 milliliter flask used and equipped as in Example 7. The reaction batch was heated and water product evolution controlled as in that example.

When 96% of the theoretical water product was collected according to Karl Fischer analysis of the evolved condensate (apparently about 60 gm. of excess acetic acid was lost along with the water), a sample of the reaction batch showed an acid value of 2.1 to allow the esterification to be considered substantially complete. The batch then was cooled to 60° and deodorized and filtered as in Example 7, yielding 329.5 gm. (89.8% theory) of the diacetate of the starting dihydroxyethyl dimethylhydantoin, having acid value 2, hydroxyl value 4.5 and saponification value 366.9.

EXAMPLE 9

"Mono"-benzoate of 1,3(dihydroxyethyl)-5,5-dimethylhydantoin (1 to 1.05 molar ratio of acid to diol)

210 gm. (1.721 moles) of benzoic acid and 390 gm. (1.815 moles) of the commercial dihydroxyethyl dimethylhydantoin of Example 1 together with 1.2 gm. of hypophosphorous acid (as 50% aqueous solution) were charged into a 1-liter, 3-necked round bottom flask equipped with stirrer, a 12-inch fractionating column with Goodloe meshed screen packing and fitted at the top with a Dean-Stark assembly designed to return a liquid oil phase including toluene azeotroping agent to the reaction flask, and provision to blanket the batch with nitrogen gas.

Heat was applied (by GLAS-COL heating jacket) with the apparatus arranged to allow substantially all of the toluene separating out (as the upper layer) in the Dean-Stark tube to be returned to the reaction batch and the esterification product water to be collected, measured, and discarded as desired. After about 90% of the theoretical water product, had been collected, samples were drawn hourly while continuing the reaction until a sample showed 1.2 acid value which indicated substantial completion of the esterification.

The toluene was distilled off and heating continued until the flask temperature came to 250°. The crude ester product was cooled to 70°, then deodorized by heating at 120° for an hour after having admixed 35% hydrogen peroxide to the extent of 0.2% by weight of the crude product. After admixing it with filter aid and filtering as in Example 1, there was obtained 527.6 gm. (92.7% of theory) of the "mono"-benzoate of the starting dihydroxyethyl dimethylhydantoin, having acid value 0.8, hydroxyl value 170.8 and saponification value 172.5.

EXAMPLE 10

Dibenzoate of 1,3-dihydroxyethyl-5,5-dimethylhydantoin (2 to 1 molar ratio of acid to diol)

311 gm. (2.55 moles) of benzoic acid, 273 gm. (1.27 moles) of the same commercial dihydroxyethyl dimethylhydantoin used in Example 1, 1.2 gm. of hypophosphorous acid (as 50% aqueous solution), and 200 milliliters of toluene (as azeotroping agent) were charged into a 1-liter flask the same, and equipped, as in Example 9. The reaction batch was heated, with the apparatus arranged, the same as in Example 9 to enable returning the separated toluene to the reaction flask and for collecting, measuring and discarding the water product.

After 93% of the theoretical water product was collected, samples of the reaction batch were taken periodically for acid value analysis until the acid value was 3.9 when the extent of the esterification was deemed satisfactory. The toluene was distilled off, the reaction batch heated to 240°, and then cooled to 70°. After admixing 35% hydrogen peroxide to the extent of 0.4% of the batch weight, the crude ester was deodorized by heating for an hour at 110°. After admixing with filter aid and filtering as in Example 1, 481 gm. (89.4% of theory) of the dibenzoate of the starting dihydroxyethyl dimethylhydantoin were obtained, having acid value 3.2, hydroxyl value 6.3 and saponification value 259.8.

EXAMPLE 11

"Mono"-oleate of 1,3-dihydroxyethyl-5,5-dimethylhydantoin (1 to 1 molar ratio of acid to diol)

339 gm. (1.21 moles) of the so-called "white oil" commercial oleic acid (average molecular weight 280) similar to that used in Example 1, and 261 gm. (1.21 moles) of the crystalline 1,3-(beta-dihydroxyethyl)-5,5-dimethylhydantoin (molecular weight 216) (prepared from the commercial grade, as illustrated by Example B below) together with 1.7 gm. of hypophosphorous acid (as 50% aqueous solution) were charged into a 1-liter, 3-necked round bottom flask equipped with stirrer, small vertical glass column connected to a horizontal water-cooled condenser, and means to provide a gentle nitrogen sparge.

The reaction batch was heated (by a GLAS-COL heating jacket) while agitating under a blanketing sparge of nitrogen for an hour and a half to 120° (when water product was evolved) and then raised in steps to 250°. After continuing heating at 250° for an additional 5½ hours, the esterification was deemed to be substantially complete when a withdrawn sample showed an acid value of 1.1. The reaction batch was cooled to 70° and, after admixing 35% hydrogen peroxide to the extent of 0.2% of the batch weight, was deodorized by heating at 110° for a half hour.

Admixture of filter aid and filtering as in Example 1 yielded 570.1 gm. (98.6% of theory) of the "mono"-oleate of the starting dihydroxyethyl dimethylhydantoin, having acid value of 1, hydroxyl value 110.4 and saponification value 121.5.

EXAMPLE 12

Dioleate of 1,3-dihydroxyethyl-5,5-dimethylhydantoin (2 to 1 molar ratio of acid to diol)

433 gm. (1.546 moles) of the "white oil" commercial oleic acid, 167 gm. (0.773 mole) of the crystalline 1,3-di(beta-hydroxyethyl)-5,5-dimethylhydantoin, both as used in Example 11, together with 1.2 gm. of hypophosphorous acid (as 50% aqueous solution) were charged into a 1-liter, 3-necked flask equipped as described in Example 11.

The reaction batch was heated under a blanketing sparge of nitrogen to about 120° until evolution of esterification water product started (as in Example 11). The esterification was continued under heating until the reaction temperature in the flask reached 250°, and after 6 hours at that temperature when a sample of the reaction batch showed an acid value of 2.6, the esterification was deemed substantially complete and was cooled to 80°. After admixing 35% hydrogen peroxide to the extent of 0.2% by weight of the reaction batch, it was deodorized by heating at 110° or 1 hour. After admixture of filter aid and filtering as in Example 1, there remained 559.3 gm. (97.7% of theory) of the dioleate of 1,3-di(beta-hydroxyethyl)-5,5-dimethylhydantoin having acid value 2.1, hydroxyl value 2.6 and saponification value 152.6.

EXAMPLE 13

"Mono"-oleate of
1—$(CH_2·CH_2O)_x·H$,3-$(CH_2·CH_2O)_y·H$—5,
5-dimethylhydantoin, wherein $x + y$ averages 16.2 (1.2 to 1 molar ratio of acid to diol)

2,420 gm. (8.64 moles) of the "white oil" commercial oleic acid as used in Example 11, and 6.080 gm. (7.21 moles) of 1—$(CH_2·CH_2O)$ x·H,3—$(CH_2·CH_2O)_y$·H—5,5-dimethylhydantoin, wherein $x + y$ averages 16.2 (average molecular weight 844, prepared as described in Example C below) together with 17 gm. of hypophorous acid (50% aqueous solution) as catalyst were charged into a 10-liter, 3-necked round bottom flask equipped with stirrer, provisions for nitrogen gas sparging, and 6-inch vertical air-cooled reflux condenser attached to a horizontal water-cooled condenser.

The reaction batch was heated (by a GLAS-COL electric heating jacket) under agitation and a gentle nitrogen sparge rate to 250° in a period of about 2 hours. After continuing the reaction at 250° for about 4 hours, the esterification was judged to be substantially complete when a sample showed the acid value to be only 1.1. The reaction batch was cooled to 70°, and then deodorized after admixing 35% hydrogen peroxide to the extent of 0.2% by weight of the batch and heating for 1 hour at 110°. After admixing filter aid as in Example 1 and filtering, 8295 gm. (99.4% of theory) of the "mono"-oleate of the starting 1,3-di(polyethoxy)dimethylhydantoin wherein $x + y$ averages 17 were obtained, with acid value 1.1., hydroxyl value 38.7 and saponification value 61.1.

EXAMPLE 14

"Mono"-stearate of
1—$(CH_2·CH_2O)_x·H$,3—$(CH_2·CH_2O)_y·H$—5,
5-dimethylhydantoin, wherein $x + y$ averages about 17 (1.1 to 1 molar ratio of acid to diol)

2,754 gm. (10.2 moles) of the 55% type commercial stearic acid as used in Examples 2 and 3 (average molecular weight 270) 8,046 gm. (9.18 moles) of 1—$(CH_2·CH_2O)_x·H$,3$(CH_2·CH_2O)_y·H$—5, 5-dimethylhydantoin, wherein $x + y$ averages 17 (average molecular weight 876, prepared as stated in Example 13), together with 16.2 gm. of hypophosphorous acid (50% aqueous solution) as catalyst were charged into a 12-liter, 3-necked round bottom flask equipped with stirrer, provision for nitrogen gas surface blanket, and a small water-cooled horizontal condenser.

The reaction batch was heated (by a GLAS-COL electric heating jacket) under agitation and nitrogen blanket to 200° in a period of 2 hours. After continuing the reaction at 200° for about 10 hours, the esterification was judged to be substantially complete. The reaction batch was cooled to 80°, and then, deodorized by heating at 110° after admixing 35% hydrogen peroxide to the extent of 0.13% by weight of the batch and containing sufficient potassium hydroxide to adjust the pH of the batch to 5.9. A diatomaceous earth clarification and filter aid was admixed and the mixture filtered yielding as filtrate 10,290 gm. (96.9% of theory) of the resulting "mono"-stearate of 1,3-di(polyethoxy)-5,5-dimethylhydantoin wherein $x + y$ averages about 17, having acid value 2.4, hydroxyl value 47.6, saponification value 54.4 and neutralization value nil.

EXAMPLE 15

Distearate of
1—$(CH_2·CH_2O)_x·H$,3—$(CH_2·CH_2O)_y·H$—5,
5-dimethylhydantoin, wherein $x + y$ averages 6.6(2 to 1 molar ratio of acid to diol)

4842 gm. (17.543 moles) of the ordinary commercial 70% stearic acid (from tallow, about 70% stearic acid, balance for the most part palmitic acid and a small amount of myristic acid; average molecular weight 276) and 3658 gm. (8.772 moles) of 1—$(CH_2·CH_2O)_x·H$,3—$(CH_2·CH_2O)_y·H$—5,5-dimethylhydantoin, wherein $x + y$ averages 6.6 (average molecular weight 417, obtained as stated in Example D below), and with 17 gm. of hypophosphorous acid (50% aqueous solution) as catalyst were charged into a 12-liter, round bottom flask equipped with a stirrer, vertical 12-inch Goodloe meshed screen packed fractionating column connected at its upper end to a water-jacketed horizontal condenser, having provisions for nitrogen gas sparge and surface blanket, and clothed with a GLAS-COL electric heating jacket.

The batch was heated over 2 hours to 240° and held there for about 16 hours when it showed an acid value of 3.9 and the esterification was deemed complete. The batch then was cooled to 70° and was deodorized by admixing 0.2% of the batch weight of 35% hydrogen peroxide and heating to 110° with steadily increasing nitrogen sparge rate and holding at 110° for an hour. The batch then was cooled again to 70° and 50% aqueous sodium hydroxide solution was added to neutralize the acid catalyst and adjust the pH to about 7.5. Diatomaceous earth filter aid was admixed to 1% of the batch weight and the still liquid crude ester product was vacuum filtered. 8075 gm. of cooled final product yield (95% of total charge) was obtained showing:

| | |
|---|---|
| color (Gardner) 1 | acid value 3.9 |
| saponif'n value 124.8 | hydroxyl value 3.1 |
| pH (of 5% sol'n) 7.2 | melting pt. 37.2° |

EXAMPLE 16

Di-laurate of
1—$(CH_2·CH_2O)_x·H$,3—$(CH_2·CH_2O)_y·H$—5,
5-dimethylhydantoin, wherein $x + y$ averages 20.9(2 to 1 molar ratio of acid to diol)

This product was prepared by esterifying 2414 gm. (11.606 moles) of lauric acid (from hydrogenated coconut oil fatty acids, average molecular weight 208) with 6086 gm. (5.802 moles) of 1—$(CH_2·CH_2O)_x·H$,3—$(CH_2·CH_2O)_y·H$—5,5-dimethylhydantoin, wherein $x + y$ averages 20.9 (average molecular weight 1049) in the same equipment as used in Example 15 and by its same procedure with its same amount of catalyst, but at esterification temperature of 245° instead of 240°.

8016 gm. of cooled final end product (94.3% of total charge) were obtained showing the following analyses:

| | |
|---|---|
| color (Gardner) under 1 | acid value 2.5 |
| saponif'n value 80.7 | hydroxyl value 4.0 |
| pH (of 5% sol'n) 6.1 | solid'n Pt. −3° |

EXAMPLE 17

"Mono"-oleate of
1—$(CH_2 \cdot CH_2O)_x \cdot H$,3—$(CH_2 \cdot CH_2O)_y \cdot H$
—5,5-dimethylhydantoin, wherein $x + y$ averages 6.6
(1.25 to 1 molar ratio of acid to diol)

6246 lbs. (22.307 moles) of the "white oil" commercial oleic acid as used in Example 11 and 7754 lbs. (18.595 moles) of 1—$(CH_2 \cdot CH_2O)_x \cdot H$,3—$(CH_2 \cdot CH_2O)_y \cdot H$—5,5-dimethylhydantoin, wherein $x + y$ averages 6.6 (average molecular weight 417), along with 20 lbs. of hypophosphorous acid (50% aqueous solution) as catalyst were charged into a 2200 gallon capacity stainless steel reactor equipped for steam and DOWTHERM heating, a vertical air-cooled type reflux condenser open at the top to the atmosphere, and with provisions for carbon dioxide sparge and surface blanket.

The reaction batch was heated to 240° and held there for about 16 hours when a sample showed its acid value to be less than 2 so that the esterification was deemed complete. The crude ester product was cooled to 70° and deodorized by admixing 28 lbs. of 35% hydrogen peroxide and while agitating heating up to 110° and holding it there for an hour while using increasing $CO_2$ sparge.

The deodorized liquid ester product was cooled to 70°, about 50 lbs. of diatomaceous earth filter aid were admixed and the batch filtered on a filter press. The clarified final end product ester yield of 13,060 lbs. (92.9% of total charge) showed the following analyses:

| | |
|---|---|
| color (Gardner) less than 1 | acid value 1.2 |
| saponif'n value 95.3 | hydroxyl value 57.0 |
| pH (5% sol'n) 6.3 | solid'n Pt. −24° |

EXAMPLE 18

"Mono"-oleate of
1—$(CH_2 \cdot CH_2O)_x \cdot H$,3—$(CH_2 \cdot CH_2O)_y \cdot H$
—5,5-dimethylhydantoin, wherein $x + y$ averages 11.8
(1.2 to 1 molar ratio of acid to diol)

4796 lbs. (17.129 moles) of the same "white oil" commercial oleic acid and 9204 lbs. (14.27 moles) of 1—$CH_2 \cdot CH_2O)_x \cdot H$,3—$(CH_2 \cdot CH_2O)_y \cdot H$—5,5-dimethylhydantoin, wherein $x + y$ averages 11.8 (average molecular weight 645, obtained as stated in Example D below) were esterified with the same weight of catalyst, in the same equipment as in, and by the same procedure of, Example 17 except that after the hydrogen peroxide deodorization, the pH of the liquid crude ester product was adjusted to about pH 6.1 with 1 lb. of sodium hydroxide (as a 50% aqueous solution). The 13,522 lbs. yield (94.7% of total charge) of final end product ester obtained showed the followed analyses:

| | |
|---|---|
| color (Gardner) less than 1 | acid value 1.1 |
| saponif'n value 70.9 | hydroxyl value 45.6 |
| pH (in 5% sol'n) 6.1 | solid'n Pt. −16° |

EXAMPLE 19

"Mono"-oleate of
1—$(CH_2 \cdot CH_2O)_x \cdot H$,3—$(CH_2 \cdot CH_2O)_y \cdot H$
—5,5-dimethylhydantoin, wherein $x + y$ averages of
16.2 (1.2 to 1 molar ratio of acid to diol)

1993 lbs. of same "white oil" commercial oleic acid (7.118 moles) and 5007 lbs. (5.932 moles) of 1—$(CH_2 \cdot CH_2O)_x \cdot H$, 3—$(CH_2 \cdot CH_2O)_y$—5,5-dimethylhydantoin, wherein $x + y$ averages 16.2 (average molecular weight 844, prepared as stated in Example D below) along with 14 lbs. of the same aqueous acid solution catalyst were reacted in a 1000 gallon stainless steel reactor equipped as in Examples 17 and 18 and by the same procedure except at an esterification temperature of 250° and until a sample showed the acid value to be less than 2 indicating completion of the esterification.

The cooled 6689 lbs. yield (94.7% of total charge) of final end product ester showed the following analyses:

| | |
|---|---|
| color (Gardner) less than 1 | acid value 1.3 |
| saponif'n value 59.8 | hydroxl value 37.0 |
| pH (of 5% sol'n) 6.2 | clear Pt. −3° |

EXAMPLE 20

"Mono"-oleate of
1—$(CH_2 \cdot CH_2O)_x \cdot H$,3—$(CH_2 \cdot CH_2O)_y \cdot H$—5-ethyl-5-methylhydantoin, wherein $x + y$ averages about 48.8
(1.2 to 1 molar ratio of acid to diol)

64 Grams (0.2286 mol) of the "white oil" commercial oleic acid (such as used in Example 11) and 436 gms. (0.19 mol) of 1—$(CH_2 \cdot CH_2O)_x \cdot H$,3—$(CH_2 \cdot CH_2O)_y \cdot H$—5-ethyl-5-methylhydantoin wherein $x + y$ averages 48.8 (prepared by the procedure of Example C below but by using 1 mol of 5-ethyl-5-methylhydantoin instead of the DMH and about 50 mols of ethylene oxide instead of the amount used in that example), together with 1 gm. of hypophosphorous acid (50% aqueous solution) as catalyst were charged into a 1 liter 3-necked round bottom flask equipped with stirrer, inlet to a sparging tube to provide a nitrogen gas blanket and a thermometer, and a 6-inch Goodloe packed column.

The reaction batch was heated (by a GLAS-COL heating jacket) under a nitrogen gas blanket (while agitating) to 240° C, in a period of about an hour. After continuing the reaction at 240° for about 5 hours and 40 minutes the reaction was allowed to cool and a sample removed showed an acid value of 3.1. The heat was turned off and the reaction was let stand till over the week end. The following Monday morning another 1 gm. of hypophosphorous acid was added, the Goodloe column removed, nitrogen gas blanket was supplied and the reaction again heated to 240° C. and the temperature then increased to 245° C. over the next 2 hours when a sample taken showed an acid value of 1.2.

The esterification then was considered to be finished. The reaction bath was allowed to cool down to about 70° C. when a gram of 30% hydrogen peroxide was admixed and the reaction batch heated to 110° C. and held at that for an hour to deodorize it. A 5% aqueous solution of the product ester had a pH of 5.5. Diatomaceous earth filter aid was admixed in the still liquid hot ester and the mixture was filtered giving 448 gms. of the end product "mono"-oleate of $1-(CH_2 \cdot CH_2O)_x \cdot H$, $3-(CH_2 \cdot CH_2O)_{y \cdot H}$—5-ethyl-5-methylhydantoin wherein $x + y$ averages about 48.8.

That 448 gms. plus 8 gms. taken as samples for the acid value tests made a total yield of 456 gms. of product ester. That is 91.9% of theoretical. The melting point of the final product ester is 36.2° C., color less than 1 (Gardner scale), hydroxyl value 15 (theoretical 17), acid value 1, saponification value 30 (theoretical 27), smoke point 310° F., flash point 540° F., fire point of 600° F.; and a 5% solution of the ester showed a pH of 4.9.

EXAMPLE 21

"Mono"-oleate of
$1-(CH_2 \cdot CH_2O)_x \cdot H, 3-(Ch_2 \cdot CH_2O)_y \cdot H-5,$
5-dimethylhydantoin wherein $x + y$ averages about 92.9 (1.2 to 1 molar ratio of acid to diol)

14.8 gms. (0.053 mol) of the "white oil" commercial oleic acid (such as used in Example 11) and 185.2 gms. (0.044 mol) of $1-(CH_2 \cdot CH_2O)_x \cdot H, 3-(CH_2O)_y \cdot H$—5,5-dimethylhydantoin wherein $x + y$ averages about 92.9 (prepared by a procedure like that of Example C below but by using 100 mols of ethylene oxide instead of the amount used in that example), together with 0.4 gm. of hypophosphorous acid (50% aqueous solution) as catalyst were charged into a 500 ml. 4-necked round bottom flask equipped with stirrer, nitrogen gas inlet to a sparge tube to provide a nitrogen gas blanket, thermometer, and a vapor take-off.

The reaction batch was heated (by a GLAS-COL heating jacket) under a nitrogen gas blanket (while agitating) to 166° C. and held there for about 20 minutes. The reaction temperature then was raised to 232° C. and held there for about 3 hours when the heat was turned off and the reaction batch was left standing overnight. The following morning the heat was started and also the nitrogen sparge, and 0.2 gm. of hypophosphorous acid (as 50% aqueous solution) was added. After the temperature reached 236° C., it was held there for about 1¾ hour and then raised to 245° C. and held there for about 4 hours and then raised and held at 250° for about a half hour.

A sample then taken showed an acid value of 0.8, and the esterification was considered to be finished. The heat was turned off. The following morning 0.4 gm. of 35% hydrogen peroxide was added and the ester product heated to 110° C. and held there for an hour to deodorize it. The 5% aqueous solution of the end product ester showed pH 4.2. Two drops of 50% aqueous sodium hydroxide solution were admixed, and a 5% aqueous solution of the product then showed pH 6.4.

While the ester product was still hot, diatomaceous earth filter aid was admixed and the mixture filtered giving the finished end product ester, "mono"-oleate of $1-(CH_2 \cdot CH_2O)_x \cdot H, 3-(CH_2 \cdot CH_2O)_y \cdot H$—5,5-dimethylhydantoin wherein $x + y$ averages 92.9. Yield was 182 gms. (91.4% of theory). Its melting point was 44.5° C., color less than 1 (Gardner scale), acid value 0.73, hydroxyl value 10 (theoretical 10), saponification value 16 (theoretical 15), and a 5% aqueous solution of it showed pH 4.2.

EXAMPLE 22

Distearate of
$1-(CH_2 \cdot CH_2 \cdot CH_2O)_x \cdot H, 3-(CH_2 \cdot CH_2O)_y \cdot H-5,5-$
dimethylhydantoin, wherein $x + y$ averages 11.5 (1.978 mole of stearic acid per mol of the ethoxylated dimethylhydantoin)

300 lbs. (1.088 mols) of so-called 70% commercial stearic acid (containing about 68% of stearic acid, 2% of margaric acid, 26.5% of palmitic acid, 0.5% of pentadecanoic acid, 2% myristic acid, and 1% of oleic acid (average molecular weight 275.6) and 350 lbs. (0.55 mol) of the ethoxylated dimethylhydantoin of the title of this example (average molecular weight 635.6) together with 2 lbs. of hypophosphorous acid (50% aqueous solution) were charged into a 100 gallon esterifier described and equipped as in Example 5.

Upon heating slowly with agitation to and at 250° C., water of esterification was evolved, and after 6.5 hours a sample of the crude ester showed a hydroxyl value of 9.7 and acid value 7.6. At this point, the esterification reaction batch was cooled and the charge was adjusted by the addition of 24 lbs. (0.038 mol) of the starting ethoxylated dimethylhydantoin and the reaction was continued at esterification temperature until a withdrawn sample showed the acid value reduced to 1.7. The batch then was cooled, bleached and filtered as described in Example 5, and there was obtained a final product having hydroxyl number of 10.2, saponification value 95.2, acid value 1.5, and melting point of 32° C.

EXAMPLE 23

"Mono"-oleate of
$1-(CH_2 \cdot CH_2O)_x \cdot H-3-(CH_2 \cdot CH_2O)_y \cdot H-5,5-$dimethylhydantoin, wherein $x + y$ averages 52.1 (1.21 mol of oleic acid per mol of ethoxylated dimethylhydantoin)

49 gms. (0.175 mol) of commercial oleic acid (average molecular weight 280, as used in Example 4) and 351 gms. (0.145 mol) of the polyethoxylated dimethylhydantoin of the title of this example (average molecular weight 2423) were admixed together with 0.8 gm. hypophosphorous acid (50% aqueous solution) as catalyst in a 1 liter, round bottom flask fitted with a gas inlet tube, stirrer, Goodloe-packed column connected to a horizontal water-cooled condenser, and thermometer.

Heating the reaction batch gently to and at 250° C. over 12 hours, with elimination of the appropriate quantity of water of esterification, resulted in the reaction product ester showing acid value of 0.8. After cooling, deodorizing bleaching, and filtering (as in others of the examples) there was obtained 369 gms. (yield 93% of theory) of the "mono"-oleate of the title of this example, showing hydroxyl value 14.3, acid value 0.66, saponification value 25.2, and smoke point 265° C.

The specific 1,3-di(polyethoxy)-5-substituted hydantoin used in any of Examples 13 through 23 can be replaced by any other starting 1,3-di(polyethoxy)-5-substituted hydantoin, wherein $x + y$ in the structural formula (of this specification page 1 lines 5–10, modified as explained at page 6 lines 7 to 25, to represent these starting N,N'-substituted hydantoins) averages any sum from 2 to 100 or, for example, within various ranges providing certain desirable products, as from about 4 to 7, or about 9 to 12, or about 14 to 17, and about 19 to 21.

So also, in Examples 13 through 19, and in any of the just described possible modifications of them, the molar ratio of the starting fatty acid to the diol can be increased to 1.5 moles of the fatty acid to 1 mole of the diol to provide the respectively corresponding sesqui esters, or increased to from about 2 to about 2.1 moles of the acid per mole of the diol to provide the respectively corresponding di-esters.

In many of the examples, including any of those foregoing modifications of Examples 13 through 19, the starting N,N'-substituted dimethylhydantoin can be replaced by the correspondingly N,N'-substituted hydantoin or any 5-mono- or di-substituted hydantoin wherein the 5-position is substituted by any of the respective substituents $R_3$ and $R_4$, represented as recited earlier above, to yield the respectively corresponding end products differently substituted at the 5-carbon or unsubstituted there.

Any of the starting dihydroxyethyl-group-containing hydantoins (whether unsubstituted or substituted in any way described in the two next proceeding paragraphs) can be prepared with the desired value for the sum of $x + y$ or average of their sum by ethoxylating the respective hydantoin or 5-mono- or di-substituted hydantoin with the respectively required number of moles of ethylene oxide by the method described at page 2 line 23 to page 6 line 6.

Thus, each such different substitution on the 5-carbon of the hydantoin ring and corresponding use of the respectively selected moles of ethylene oxide provides a further example, which is to be considered as if written out in full herein to show and give the preparation of the corresponding ester of the selected fatty acid with the respective 1,3-dihydroxyethyl or 1,3-dihydroxyethoxyethyl or 1,3-dihydroxyethoxypolyethoxyethyl-hydantoin with respectively correspondingly different substitution on the 5-carbon, in each of which the amide nitrogen is in the 1-position and the imide nitrogen in the 3-position, including, for example, 1,3-dihydroxyethyl-5-methylhydantoin,
1,3-bis(beta-hydroxyethyl)-5-ethylhydantoin,
1,3-bis(beta-hydroxyethyl)-5-propylhydantoin,
1-(ethoxy)$_x$-H3-(ethoxy)$_y$-H-5-methyl hydantoin, wherein $x + y$ averages from 2 to about 70 or even about 100,
1,3-bis(beta-hydroxyethyl)-5-methyl,5-ethoxyethyl-hydantoin,
1,3-bis(beta-hydroxyethyl)-5,5-spiro-tetramethylenehydantoin;

and many others with any of the other of the earlier above disclosed possible 5-position substituents.

In any of Examples 1 through 10 and 13 through 19 and any of the just earlier above described modifications of any of them, the starting commercial grade of the specific hydantoin diol can be replaced by the crystalline grade of the diol such as that used in Examples 11 and 12 or any modification of each of them otherwise substituted (as earlier above described) on the 5-carbon or unsubstituted there or by any of them otherwise polyethoxylated (within the earlier above disclosed range) on either or both of the ring nitrogens.

The starting commercial grades of the fatty acids obtained from animal material sources (for example, tallow or fats) or vegetable sources (for example, coconut oil or the well known seed oils as cotton seed oil and soybean oil) contain a mixture of fatty acids. Thus, the end products, for example, of Examples 1 to 5 and 11 to 19 obviously actually contain a mixture of fatty acid esters of the respective fatty diol used, and the ester formed with the respective fatty acid which is the major constituent of the starting commercial grade of fatty acid predominates in the mixed esters end product of the example along with lower amounts of the esters of the other fatty acids found in the starting mixture of them and substantially proportionate to their respective content in the commercial grade fatty acid. Thst is the same as the situation that occurs in the case of the caprate and caprylate mixture end product of Example 6.

Then, any of these starting commercial grades of stearic acid, oleic acid or lauric acid used in any of the Examples 1 to 5 and 11 to 19, or the mixture of capric and caprylic acids of Example 6, may be replaced by any other differently quantitatively composed grades or blended modifications of them to provide the respectively corresponding mixed ester products. Similarly, any of these starting mixtures of the fatty acids can be replaced respectively by any one of the individual fatty acids having from 2 to about 22 carbons as illustrated by the use of acetic acid as in Examples 7 and 8.

Thus, for example, replacing the commercial stearic acid mixture used in any of Examples 2, 3, 14 and 15 and any of the shortly earlier above described modifications of them, by the respectively corresponding molar quantity of substantially pure stearic acid, there is obtained the corresponding ester end product wherein the acyl moiety is solely stearic acid.

Similarly, any of the other commercial fatty acid mixtures can be replaced by the substantially pure fatty acid that predominates in it, for example, with lauric acid replacing the commercial hydrogenated coconut fatty acids in Example 5, thereby providing the corresponding ester end product wherein the acyl moiety is solely that of the respective fatty acid such as lauric acid.

The same can be done with either of the capric acid and the caprylic acid of Example 6 to provide the corresponding esters wherein the acyl moiety is solely that of capric acid or caprylic acid respectively. Then too, as in Examples 11 and 12, the commercial N,N'-dihydroxyethyl-dimethylhydantoin of any of the other examples or any of the shortly above indicated modifications of them likewise can be replaced by the crystalline 1,3-dihydroxyethyl-5,5-dimethylhydantoin, as used in Examples 11 and 12, to give with the selected pure fatty acid in each case the respectively corresponding ester resulting from the esterification with the pure fatty acid.

In any event, even with the use of the purified grade of either one or both of the primary reactants, when the mono-ester is prepared, just as in Examples 4, 5, 7, 9, 11, 13 and 14, the end product is a mixture of the 1-mono-ester, the 3-mono-ester, and the 1,3-di-ester, with the total of both mono-esters by far predominating over the proportion of di-ester, with unreacted diol equivalent to about one-half of the molar content of the di-ester.

To avoid unduly extending the length of this specification and its becoming prolix, it is to be understood that each of the separate individual end product esters resulting from each of the foregoing described possible modifications of the Examples 1 to 19 be considered as if incorporated herein as written out in full as a separate additional example.

The respective starting 5,5-dimethylhydantoin diols of certain of the examples are obtained as shown in the following examples:

EXAMPLE A

Commercial 1,3-bis(beta-hydroxyethyl)-5,5-dimethylhydantoin for Example 7

A mixture of 12 lbs. each of 5,5-dimethylhydantoin (DMH, 0.095 mole) and 1,4-dioxane and 0.12 lb. of 45% potassium hydroxide aqueous solution (as catalyst) were heated in a jacketed 5-gallon Doyle-Roth autoclave (equipped with agitator and liquid feed inlet) to dissolve the DMH, with the autoclave purged with nitrogen. The resulting solution then was heated to 95°, the pressure vented off to the atmosphere, and then heated to 120°.

With the vent closed, heating was continued to hold the temperature between 120° and 140° while ethylene oxide automatically intermittently was fed into the autoclave through an automatic pressure-controlled valve allowing feeding when the internal pressure dropped to 60 lbs./sq. inch gauge (i.e. psig.) and turning off the flow when the pressure reached 61 psig., until over a 2 hour period a total 8.35 lbs. (0.19 mole) of ethylene oxide were added at the maintained temperature range. When the last of the ethylene oxide was consumed, the pressure dropped sharply.

The batch then cooled to about 80° was transferred to a 2 liter 3-necked distilling flask and mixed for about 15 minutes after neutralizing the catalyst with the required amount of 85% phosphoric acid. The dioxane was recovered by distillation at 140° under vacuum (5 mm. Hg.). Filtering the liquid still residue yielded the light yellow viscous filtrate commercial 1,3-bis(betahydroxyethyl)-DMH with the following gas liquid chromatography (GLC) analysis:

| | |
|---|---|
| 1,3-bis(beta-hydroxyethyl)DMH | 84.6%, |
| monohydroxyethyl DMH (a mixture of the 1- and 3-isomers with the latter predominating | 8.5%, |
| triethoxylated DMH (a mixture of 1-hdroxyethoxyethyl,3-hydroxyethyl DMH and of 1-hydroxyethyl,3-hydroxyethoxyethyl DMH, with the latter isomer predominating | 5.5%, |
| tetraethoxylated DMH with x + y averaging 4 (a mixture of 1-hydroxyethyl,3-hydroxyethoxyethoxyethyl DMH, and 1-hydroxyethoxyethoxyethyl, 3-hydroxyethyl DMH, and 1,3-bis(beta-hydroxyethoxyethyl) DMH, with the last of them predominating) | 0.6%, and |
| DMH | 0.8%. |

Repeating Example A but increasing the ethylene oxide to a molar equivalent of 2.2 moles of it per mole of starting DMH provided the viscous liquid final product filtrate with GLC analysis:

| | |
|---|---|
| 1,3-bis(beta-hydroxyethyl)DMH | 82.6%, |
| monohydroxyethyl DMH (same mixture as in first run) | 1.8%, |
| triethoxylated DMH (same mixture as in first run) | 14.7%, and |
| tetraethoxylated DMH (same mixture as in first run) | 0.9%. |

EXAMPLE B

Crystalline 1,3-bis(beta-hydroxyethyl)DMH for Examples 11–12

250 gms. of the viscous liquid filtrate product of Example A dissolved at ambient temperature in a mixture of 62.5 gms. of isopropyl alcohol in 1187.5 gms. of benzene was seeded with a trace of crystalline 1,3-bis(-beta-hydroxyethyl)DMH (obtained by crystallization of a 20 gm. viscous liquid product from the same solvent mixture). The solution turned opalescent and separated a layer of crystals almost as soon as its container was placed into a water-bath at 11°. Four days later the crystals were removed by suction filtration on a Buchner funnel, and vacuum dried in a rotary vacuum drier at atmospheric pressure. No further crystals separated from the filtrate when its container was returned to the 11° water-bath, and even on the following day. GLC analysis of the crystals showed:

| | |
|---|---|
| 1,3-bis(beta-hydroxyethyl)DMH | 97.9%, |
| monohydroxyethyl DMH | 0.8%, |
| triethoxylated DMH | 0.8%, |
| tetraethoxylated DMH | 0.1%, and |
| unreacted DMH | 0.4%. |

Each of these mono-, tri-, and tetra-ethoxylated components included a mixture of its respectively same isomers as in Example A.

EXAMPLE C

The x + y averages about 17 ethoxylated DMH, of Example 13

By the procedure of Example A, 128 parts (1 mole) of DMH were heated and dissolved in 354 parts of dioxane and 2.48 parts of KOH 45% aqueous solution. Then 748 parts (17 moles) of ethylene oxide were automatically intermittently fed into the autoclave over about 6 hours with the pressure maintained between about 50 to 55 psig. and temperature held at about 140°. The reaction batch, after cooling, was removed to a distillation flask, neutralized with 1.15 parts of 85% phosphoric acid and the solvent stripped off, leaving behind the clear viscous light yellow liquid ethoxylated DMH with x + y averaging about 17.

Similarly the starting ethoxylated DMH with x + y averaging about 20 for Example 16 is prepared as in Example C but using instead about 400 parts of dioxane, 2.6 parts of 45% aqueous KOH and 880 parts (20 moles) of ethylene oxide fed over about 7 hours, and neutralizing the KOH catalyst with 1.2 parts of 85% phosphoric acid.

EXAMPLE D

The ethoxylated DMH with $x + y$ averaging 6.6, of Examples 15 and 17

This was prepared as in Example C but instead using 128 parts of dioxane, 0.65 parts of the 45% aqueous KOH, and similarly feeding in 289 parts (6.7 moles) of ethylene oxide over about 3 hours and maintaining pressure between 45 to 50 psig. at about 140°; and after cooling the reaction batch and removing it to the distilling flask, neutralizing it with 0.3 parts of the 85% phosphoric acid and stripping off the solvent.

The starting ethoxylated DMH with $x + y$ averaging 11.8 for Example 18 was prepared as in Example D but using instead 1.3 parts of 45% aqueous KOH and 517 parts (11.8 moles) of ethylene oxide fed over 4 hours and 15 minutes, and neutralizing the KOH with 0.6 parts of 85% phosphoric acid.

All temperatures throughout are in centigrade.

The "white oil" commercial oleic acid used in the similar starting material in Examples 1, 4, 11 to 13 and 17 to 19 is called "white oleine", provided generally by the at least double distillation of the crude oleic acid, called "red oil", as obtained from the usual sources such as tallow and the various animal fats. The 80 to about 88.5% white oil (commercial oleic acid) used in these examples analyzed about 72.5% 9-cis-octadecenoic acid, 8.6% linoleic acid, 5.7% palmitoleic acid, 1.4% myristoleic acid, 0.9% stearic acid, 2.1% hepadecanoic acid, 5% palmitic acid, 3.2% myristic acid and 0.5% lauric acid.

The expression "total oleic acids" (of page 7 line 16 above) is that ordinarily used in the fatty acids industry to include the total of the separate quantities of oleic acid, linoleic acid, linolenic acid, palmitoleic acid and myristoleic acid that occur in varying, often closely similar respective, amounts in the various white oil commercial grades of oleic acid obtained from their various common sources.

The starting commercial grade stearic acid is the same in all of Examples 2, 3, 14 and 15. The lauric acid from hydrogenated coconut oil fatty acids used in Example 16 and the commercial hydrogenated coconut fatty acids of Example 5 are the same lauric acid-containing reactant. Each of any of the other available commercial lauric acid, oleic acid, or stearic acid (e.g. the so-called 70/30) grades can be used respectively similarly.

Because these various available commercial grades of certain of these fatty acids used contain one of them as the major constituent of what is a mixture of that one respective major constituent fatty acid and the others accompanying it, the ester end products obtained in Examples 1 to 6 and 11 to 19 actually are mixtures of esters.

The prefix "mono" is enclosed within quotation marks in, for example, the titles of Examples 4, 6, 7, 9, 11, 13, 14 and 17 to 19, wherein the acid and diol charges are in substantially equimolar ratio, because the respective end product ester in them actually is not a single ester wherein the acyl group is linked solely to one of the nitrogens. Instead, these separate end products of these examples consist of a major part of both of the mono-esters wherein in one of them the acyl groups are linked to the 1-nitrogen and in the other of them are linked to the 3-nitrogen, with the minor part being the di-ester, and when the molar ratio of the starting fatty acid sometimes, for example, as in Examples 4 and 6, is slightly lower than that of the starting hydantoin diol, then also with the correspondingly small amount of unreacted diol.

The polyethoxylated dimethylhydantoin used in Example 22 can be prepared by the method of Example D below, and that used in Example 23 can be prepared by the method of Example C below. Any other starting ethoxylated or polyethoxylated hydantoin required for any of the hereinabove described modifications of any of the Examples 1 through 23 can be prepared by the general procedure described herein above for preparing these starting hydantoins and as exemplified by Examples A to D herein.

While the invention has been explained by detailed description of certain specific embodiments of it, it is understood that various changes or substitutions may be made in any of them within the scope of the appended claims which are intended also to cover equivalents of the various embodiments.

What is claimed is:

1. Esters of 1,3-dihydroxyethyl group-containing-hydantoins having the structural formula

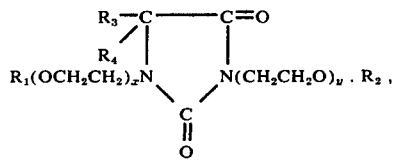

wherein each of $R_3$ and $R_4$ separately is hydrogen, lower alkyl, cycloalkyl, or alkoxy and when either or each of $R_3$ and $R_4$ is alkyl, cycloalkyl or alkoxy, they jointly have at most 7 carbons, or $R_3$ and $R_4$ jointly are the divalent tetramethylene or pentamethylene chain; either one of $R_1$ and $R_2$ is hydrogen, and the other one or each of them is benzoyl, isostearoyl, oleoyl, linoleoyl, linolenoyl, or saturated fatty acyl having from 2 to about 22 carbons or a mixture of saturated fatty acyl groups having from 8 to about 22 carbons or a mixture of any of said saturated fatty acyl groups with any of oleoyl, linoleoyl and linolenoyl, palmitoleoyl and myristoleoyl; and each of $x$ and $y$ varies from each of them being 1 to their sum averaging from 2 to about 100; and mixtures of any of said esters.

2. The esters or mixtures of them as claimed in claim 1, wherein each of $R_3$ and $R_4$ is methyl and each of $x$ and $y$ varies from each of them being 1 to their sum averaging from 2 to about 20.

3. The esters or mixtures of them as claimed in claim 2, wherein each of $R_3$ and $R_4$ is methyl and each of $x$ and $y$ is 1.

4. A mixture of esters as claimed in claim 3, wherein each of $R_1$ and $R_2$ is a mixture of the acyl groups of the fatty acids contained in the commercial white oil grade of oleic acid.

5. A mixture of esters as claimed in claim 4, wherein from about 80 to about 88.5 percent of the acyl groups $R_1$ and $R_2$ are those of the total "oleic" acids of that commercial oleic acid and the remainder of the acyl groups are those of the saturated fatty acids of that commercial oleic acid.

6. A mixture of esters as claimed in claim 5, wherein the commercial white oil grade of oleic acid consists essentially of about 72.5% of 9-cis-octadecenoic acid, about 8.6% of linoleic acid, about 5.7% of palmitoleic acid, about 1.4% of myristoleic acid, about 0.9% of stearic acid, about 2.1% of heptadecanoic acid, about 5% of palmitic acid, about 3.2% of myristic acid and about 0.5% of lauric acid.

7. The esters or mixtures of them as claimed in claim 2, wherein the sum of $x$ and $y$ averages from about 5 to about 20.

8. A mixture of esters as claimed in claim 7, wherein each of $R_1$ and $R_2$ is a mixture of the acyl groups of the fatty acids contained in one of (a) the commercial grade hydrogenated coconut oil fatty acids, (b) the commercial grade stearic acid, or (c) commercial white oil grade of oleic acid.

9. A mixture of esters as claimed in claim 8, wherein each of $R_1$ and $R_2$ is a mixture of the acyl groups contained in the commercial grade of the hydrogenated coconut oil fatty acids containing about 55% lauric acid, about 15% myristic acid, about 8% each of stearic acid and palmitic acid, about 7% caprylic acid, about 6% capric acid, and about 1% oleic acid.

10. A mixture of esters claimed in claim 9, wherein the sum of $x$ and $y$ averages from about 19 to 22.

11. A mixture of esters as claimed in claim 8, wherein each of $R_1$ and $R_2$ is a mixture of the acyl groups of the fatty acids of the commercial white oil grade of oleic acid, and the ester content has (a) as its major portion the two mono-esters (i) the one wherein $R_2$ is hydrogen and (ii) the one wherein $R_1$ is hydrogen, and (b) as its minor portion the di-ester having these acyl groups as each of $R_1$ and $R_2$ and, when the molar ratio of the total of the acyl groups of the mono-ester and the di-ester to that of the hydantoin moiety is less than one, then together with the correspondingly small residual unreacted starting hydantoin.

12. A mixture of esters as claimed in claim 11, wherein the sum of $x$ and $y$ averages from about 4 to 7, and the minor portion of the ester content consists essentially of said di-ester.

13. A mixture of esters as claimed in claim 11, wherein the sum of $x$ and $y$ averages from about 9 to 12, and the minor portion of the ester content consists essentially of said di-ester.

14. A mixture of esters as claimed in claim 11, wherein the sum of $x$ and $y$ averages from about 14 to 17, and the minor portion of the ester content consists essentially of said di-ester.

15. A mixture of esters as claimed in claim 8, wherein from about 80 to about 88.5 percent of the acyl groups $R_1$ and $R_2$ are those of the total "oleic" acids of that commercial oleic acid and the remainder of the acyl groups are those of the saturated fatty acids of that commercial oleic acid.

16. A mixture of esters as claimed in claim 15, wherein the commercial white oil grade of oleic acid consists essentially of about 72.5% of 9-cis-octadecenoic acid, about 8.6% of linoleic acid, about 5.7% of palmitoleic acid, about 1.4% of myristoleic acid, about 0.9% of stearic acid, about 2.1% of heptadecanoic acid, about 5% of palmitic acid, about 3.2% of myristic acid and about 0.5% of lauric acid.

17. A mixture of esters as claimed in claim 3, wherein each of $R_1$ and $R_2$ is a mixture of the acyl groups contained in a commercial grade of hydrogenated coconut oil fatty acids.

18. A mixture of esters as claimed in claim 17, wherein said mixture of said acyl groups contains about 55% lauric acid, about 15% myristic acid, about 8% each of stearic acid and palmitic acid, about 7% caprylic acid, about 6% capric acid, and about 1% oleic acid.

19. A mixture of esters as claimed in claim 8, wherein said mixture of acyl groups is that of the fatty acids of a commercial grade of stearic acid.

20. A mixture of esters as claimed in claim 19, wherein the sum of $x$ and $y$ averages from about 8 to about 12.

21. A mixture of esters as claimed in claim 20, wherein the sum of $x$ and $y$ averages about 11.5.

22. A mixture of esters as claimed in claim 21, wherein said commercial grade of stearic acid is the so-called 70% commercial stearic acid.

23. A mixture of esters as claimed in claim 22, wherein said 70% commercial stearic acid contains about 68% of stearic acid, 2% of margaric acid, 26.5% of palmitic acid, 0.5% pentadecanoic acid, 2% of myristic acid, and 1% of oleic acid.

24. A mixture of esters as claimed in claim 4, wherein said acyl groups are those of the fatty acids of a commercial white oil grade of oleic acid and the molar ratio of the total of the acyl groups to that of the ethoxylated hydantoin moiety is about 2 to 1.

25. A mixture of esters as claimed in claim 24, wherein from about 80 to about 88.5 percent of said acyl groups are those of the total "oleic" acids of said commercial oleic acid.

26. A mixture of esters as claimed in claim 11, wherein the molar ratio of the total of the acyl groups to that of the ethoxylated hydantoin moiety is from about 1 to about 2 moles of acyl groups per mol of said hydantoin moiety.

27. A mixture of esters as claimed in claim 26, wherein the sum of $x$ and $y$ averages from about 4 to 7.

28. A mixture of esters as claimed in claim 27, wherein the sum of $x$ and $y$ averages about 6.6.

29. A mixture of esters as claimed in claim 26, wherein the sum of $x$ and $y$ averages from about 9 to 12.

30. A mixture of esters as claimed in claim 29, wherein the sum of $x$ and $y$ averages about 11.8.

31. A mixture of esters as claimed in claim 26, wherein the sum of $x$ and $y$ averages from about 14 to 17.

32. A mixture of esters as claimed in claim 31, wherein the sum of $x$ and $y$ averages about 16.2.

* * * * *